US010216100B2

(12) United States Patent
Saeed et al.

(10) Patent No.: US 10,216,100 B2
(45) Date of Patent: Feb. 26, 2019

(54) INSPECTION SUBSTRATE AND AN INSPECTION METHOD

(71) Applicant: ASML Netherlands B.V., Veldhoven (NL)

(72) Inventors: Seerwan Saeed, Veldhoven (NL); Petrus Martinus Gerardus Johannes Arts, Echt (NL); Harold Sebastiaan Buddenberg, Sittard (NL); Erik Henricus Egidius Catharina Eummelen, Veldhoven (NL); Giovanni Luca Gattobigio, Eindhoven (NL); Floor Lodewijk Keukens, Turnhout (BE); Ferdy Migchelbrink, Veldhoven (NL); Jeroen Arnoldus Leonardus Johannes Raaymakers, Oirschot (NL); Arnoldus Johannes Martinus Jozeph Ras, Mierlo (NL); Gheorghe Tanasa, Eindhoven (NL); Jimmy Matheus Wilhelmus Van De Winkel, Kessel (NL); Daan Daniel Johannes Antonius Van Sommeren, Beuningen (NL); Marijn Wouters, Utrecht (NL); Miao Yu, Best (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

(21) Appl. No.: 15/738,701

(22) PCT Filed: Jun. 16, 2016

(86) PCT No.: PCT/EP2016/063961
§ 371 (c)(1),
(2) Date: Dec. 21, 2017

(87) PCT Pub. No.: WO2017/008993
PCT Pub. Date: Jan. 19, 2017

(65) Prior Publication Data
US 2018/0181004 A1    Jun. 28, 2018

(30) Foreign Application Priority Data

Jul. 16, 2015    (EP) .................................... 15177120

(51) Int. Cl.
*G01N 21/00* (2006.01)
*G03F 7/20* (2006.01)
(Continued)

(52) U.S. Cl.
CPC ....... *G03F 7/7085* (2013.01); *G01N 21/9515* (2013.01); *G03F 7/7065* (2013.01);
(Continued)

(58) Field of Classification Search
CPC ...... H01L 22/34; H01L 22/12; G01N 21/9501
(Continued)

(56) References Cited

U.S. PATENT DOCUMENTS 5,444,637 A   8/1995 Smesny et al.
6,140,833 A   10/2000 Flietner et al.
(Continued)

FOREIGN PATENT DOCUMENTS

CN    2720414 Y    8/2005
CN    104058361 A    9/2014
(Continued)

OTHER PUBLICATIONS

International Search Report and Written Opinion of the International Searching Authority directed to related International Patent Application No. PCT/EP2016/063961, dated Oct. 6, 2016; 10 pages.
(Continued)

*Primary Examiner* — Hoa Pham
(74) *Attorney, Agent, or Firm* — Sterne, Kessler, Goldstein & Fox P.L.L.C.

(57) ABSTRACT

An inspection substrate for inspecting a component, such as a liquid confinement system, of an apparatus for processing production substrates is discussed. The inspection substrate includes a body having dimensions similar to a production substrate so that the inspection substrate is compatible with the apparatus, an illumination device, such as light emitting diodes, embedded in the body, a sensor, such as an imaging device or a pressure sensor, that is embedded in the body and configured to generate inspection information, such as image data, relating to a parameter of the component of the apparatus proximate to the inspection substrate, and a storage device embedded in the body and configured to store the inspection information.

7 Claims, 8 Drawing Sheets

(51) Int. Cl.
  *H01L 21/66* (2006.01)
  *G01N 21/95* (2006.01)
  *H01L 27/146* (2006.01)
  *H01L 27/148* (2006.01)

(52) U.S. Cl.
  CPC ...... *G03F 7/70341* (2013.01); *G03F 7/70916* (2013.01); *H01L 22/12* (2013.01); *H01L 27/14627* (2013.01); *H01L 27/14678* (2013.01); *H01L 27/14862* (2013.01)

(58) Field of Classification Search
  USPC ........... 356/601–623, 237.1–237.5; 118/712; 438/14; 156/345.24
  See application file for complete search history.

(56) References Cited

U.S. PATENT DOCUMENTS

| | | |
|---|---|---|
| 6,191,394 B1 | 2/2001 | Shirakawa et al. |
| 2002/0109590 A1 | 8/2002 | Parsons |
| 2003/0001083 A1 | 1/2003 | Corrado et al. |
| 2003/0115956 A1 | 6/2003 | Moehnke et al. |
| 2003/0223057 A1 | 12/2003 | Ramsey et al. |
| 2004/0031340 A1 | 2/2004 | Renken |
| 2004/0098216 A1 | 5/2004 | Ye et al. |
| 2004/0154417 A1 | 8/2004 | Renken et al. |
| 2004/0207824 A1 | 10/2004 | Lof et al. |
| 2005/0062121 A1 | 3/2005 | Toyoda |
| 2005/0081398 A1 | 4/2005 | Sun et al. |
| 2005/0267606 A1 | 12/2005 | Bartlett, Jr. et al. |
| 2005/0284570 A1 | 12/2005 | Doran et al. |
| 2005/0288893 A1 | 12/2005 | Gassner |
| 2006/0015294 A1 | 1/2006 | Yetter, Jr. et al. |
| 2006/0052969 A1 | 3/2006 | Hunt et al. |
| 2006/0171848 A1 | 8/2006 | Roche et al. |
| 2006/0234398 A1 | 10/2006 | Glushenkov et al. |
| 2006/0249729 A1 | 11/2006 | Mundt et al. |
| 2007/0107523 A1 | 5/2007 | Galewski |
| 2007/0113652 A1 | 5/2007 | Renken |
| 2007/0189659 A1* | 8/2007 | Shau ................. G02B 6/12002 385/14 |
| 2007/0194913 A1 | 8/2007 | Yokoshima et al. |
| 2007/0224712 A1 | 9/2007 | Kaushal et al. |
| 2007/0243794 A1 | 10/2007 | Mundt |
| 2008/0087069 A1 | 4/2008 | Renken et al. |
| 2008/0204678 A1 | 8/2008 | DiBiase et al. |
| 2008/0228430 A1 | 9/2008 | Bonciolini et al. |
| 2009/0059217 A1 | 3/2009 | Okita |
| 2009/0085031 A1 | 4/2009 | Matsuda et al. |
| 2009/0292491 A1 | 11/2009 | Fukuoka |
| 2012/0074514 A1 | 3/2012 | Nguyen et al. |
| 2012/0084059 A1 | 4/2012 | Akada |
| 2014/0072452 A1 | 3/2014 | Tahmassebpur et al. |

FOREIGN PATENT DOCUMENTS

| | | |
|---|---|---|
| DE | 10314150 A1 | 10/2004 |
| EP | 1420298 A2 | 5/2004 |
| EP | 2131241 A1 | 12/2009 |
| JP | 2007-324308 A | 12/2007 |
| WO | WO 99/49504 A1 | 9/1999 |

OTHER PUBLICATIONS

International Preliminary Report on Patentability directed to related International Patent Application No. PCT/EP2016/063961, dated Jan. 16, 2018; 6 pages.

"Thin Film sensor on a Substrate for Immersion Diagnostics," Research Disclosure No. 581053, Aug. 27, 2012; 4 pages.

* cited by examiner

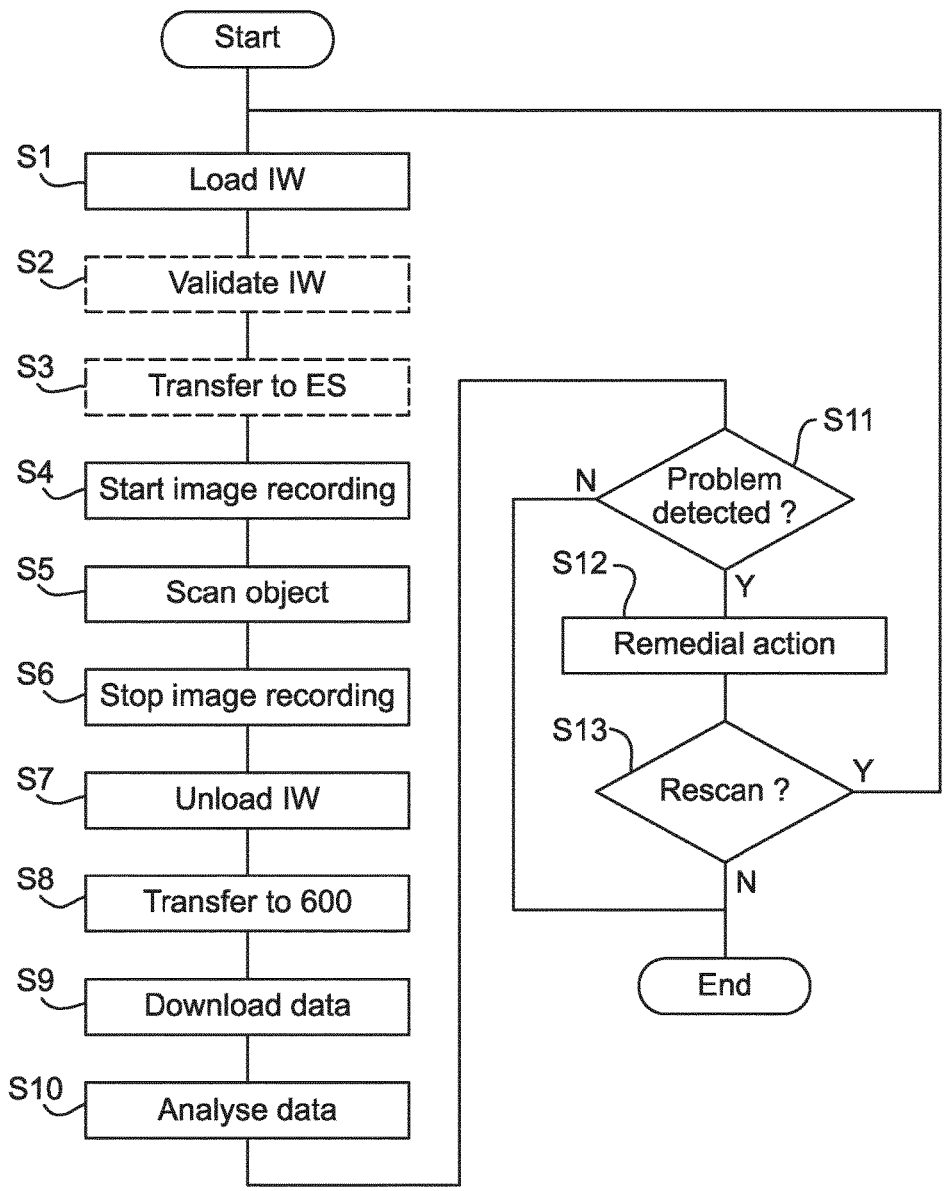

INSPECTION SUBSTRATE AND AN INSPECTION METHOD

CROSS-REFERENCE TO RELATED APPLICATIONS

This application claims priority of EP application 15177120.1 which was filed on Jul. 16, 2015 and which is incorporated herein in its entirety by reference.

FIELD

The present invention relates to an inspection substrate and an inspection method for use in a lithographic apparatus, metrology apparatus or a process apparatus, for example.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g. comprising part of, one, or several dies) on a substrate (e.g. a silicon wafer). Transfer of the pattern is typically via imaging onto a layer of radiation-sensitive material (resist) provided on the substrate. In general, a single substrate will contain a network of adjacent target portions that are successively patterned.

Immersion techniques have been introduced into lithographic systems to enable improved resolution of smaller features. In an immersion lithographic apparatus, a liquid layer of a liquid having a relatively high refractive index is interposed in a space between a projection system of the apparatus (through which the patterned beam is projected towards the substrate) and the substrate. The liquid covers at last the part of the wafer under the final lens element of the projection system. Thus, at least the portion of the substrate undergoing exposure is immersed in the liquid. The effect of the immersion liquid is to enable imaging of smaller features since the exposure radiation will have a shorter wavelength in the liquid than gas. (The effect of the liquid may also be regarded as increasing the effective numerical aperture (NA) of the system and also increasing the depth of focus.)

In commercial immersion lithography, the liquid is water. Typically the water is distilled water of high purity, such as Ultra-Pure Water (UPW) which is commonly used in semiconductor fabrication plants. In an immersion system, the UPW is often purified and it may undergo additional treatment steps before supply to the immersion space as immersion liquid. Other liquids with a high refractive index can be used besides water can be used as the immersion liquid, for example: a hydrocarbon, such as a fluorohydrocarbon; and/or an aqueous solution. Further, other fluids besides liquid have been envisaged for use in immersion lithography.

In this specification, reference will be made in the description to localized immersion in which the immersion liquid is confined, in use, to the space between the final lens element and a surface facing the final element. The facing surface is a surface of substrate or a surface of the supporting stage (or substrate table) that is co-planar with the substrate surface. (Please note that reference in the following text to surface of the substrate W also refers in addition or in the alternative to a surface of the substrate table, unless expressly stated otherwise; and vice versa). A fluid handling structure present between the projection system and the stage is used to confine the immersion to the immersion space. The space filled by liquid is smaller in plan than the top surface of the substrate and the space remains substantially stationary relative to the projection system while the substrate and substrate stage move underneath.

Other immersion systems have been envisaged such as an unconfined immersion system (a so-called 'All Wet' immersion system) and a bath immersion system. In an unconfined immersion system, the immersion liquid covers more than the surface under the final element. The liquid outside the immersion space is present as a thin liquid film. The liquid may cover the whole surface of the substrate or even the substrate and the substrate stage co-planar with the substrate. In a bath type system, the wafer is fully immersed in a bath of liquid.

The fluid handling structure is a structure which supplies liquid to the immersion space, removes the liquid from the space and thereby confines liquid to the immersion space. It includes features which are a part of a fluid supply system. The arrangement disclosed in PCT patent application publication no. WO 99/49504 is an early fluid handling structure comprising pipes which either supply or recover liquid from the space and which operate depending on the relative motion of the stage beneath the projection system. In more recent designs, a fluid handling structure extends along at least a part of a boundary of the space between the final element of the projection system and the substrate table WT or substrate W, so as to in part define the space.

The fluid handling structure may have a selection of different functions. Each function may be derived from a corresponding feature that enables the fluid handling structure to achieve that function. The fluid handling structure may be referred to by a number of different terms, each referring to a function, such as barrier member, seal member, fluid supply system fluid removal system, liquid confinement structure, etc.

As a barrier member, the fluid handling structure is a barrier to the flow of the immersion liquid from the space. As a liquid confinement structure, the structure confines liquid to the space. As a seal member, sealing features of the fluid handling structure form a seal to confine liquid to the space. The sealing features may include an additional gas flow from an opening in the surface of the seal member, such as a gas knife.

In an embodiment the fluid handling system may supply immersion fluid and therefore be a fluid supply system.

In an embodiment the fluid handling system may at least partly confine immersion fluid and thereby be a fluid confinement system.

In an embodiment the fluid handling system may provide a barrier to immersion fluid and thereby be a barrier member, such as a fluid confinement structure.

In an embodiment the fluid handling system may create or use a flow of gas, for example to help in controlling the flow and/or the position of the immersion fluid.

The flow of gas may form a seal to confine the immersion fluid so the fluid handling structure may be referred to as a seal member; such a seal member may be a fluid confinement structure.

In an embodiment, immersion liquid is used as the immersion fluid. In that case the fluid handling system may be a liquid handling system. In reference to the aforementioned description, reference in this paragraph to a feature defined with respect to fluid may be understood to include a feature defined with respect to liquid.

A lithographic apparatus is a complex apparatus and most of its critical parts have to be operated under very controlled environments, with higher contamination specifications than standard for cleanrooms. If the apparatus has to be opened up for maintenance or inspection, time consuming processes such as decontamination and start-up may need to be taken before the apparatus can be returned to service. It is desirable that any downtime of the apparatus be minimized as far as possible since this reduces the productivity of the apparatus and increases cost of ownership.

SUMMARY

It is desirable, for example, to provide means to enable critical parts of the apparatus to be inspected with minimum downtime.

According to an aspect, there is provided an inspection substrate for inspecting a component of an apparatus for processing production substrates, the inspection substrate comprising:

a body having dimensions similar to a production substrate so that the inspection substrate is compatible with the apparatus;

a sensor for generating inspection information relating to a parameter of a component of the apparatus proximate to the inspection substrate, the sensor embedded in the body; and a storage device embedded in the body, the storage device configured to store the inspection information.

According to an aspect, there is provided a method of inspecting a component of an apparatus for processing production substrates, the method comprising:

loading into the apparatus an inspection substrate having dimensions similar to a production substrate so that the inspection substrate is compatible with the apparatus, the inspection substrate having a body, a sensor and a storage device, the sensor and the storage device being embedded in the body;

scanning the inspection substrate proximate the component whilst operating the sensor to generate inspection information relating to a parameter of the component; and storing the inspection information in the storage device.

BRIEF DESCRIPTION OF THE DRAWINGS

Embodiments of the invention will now be described, by way of example only, with reference to the accompanying schematic drawings in which corresponding reference symbols indicate corresponding parts, and in which:

FIG. 13 is a flow diagram of a method according to the invention.

DETAILED DESCRIPTION

Figure 1:
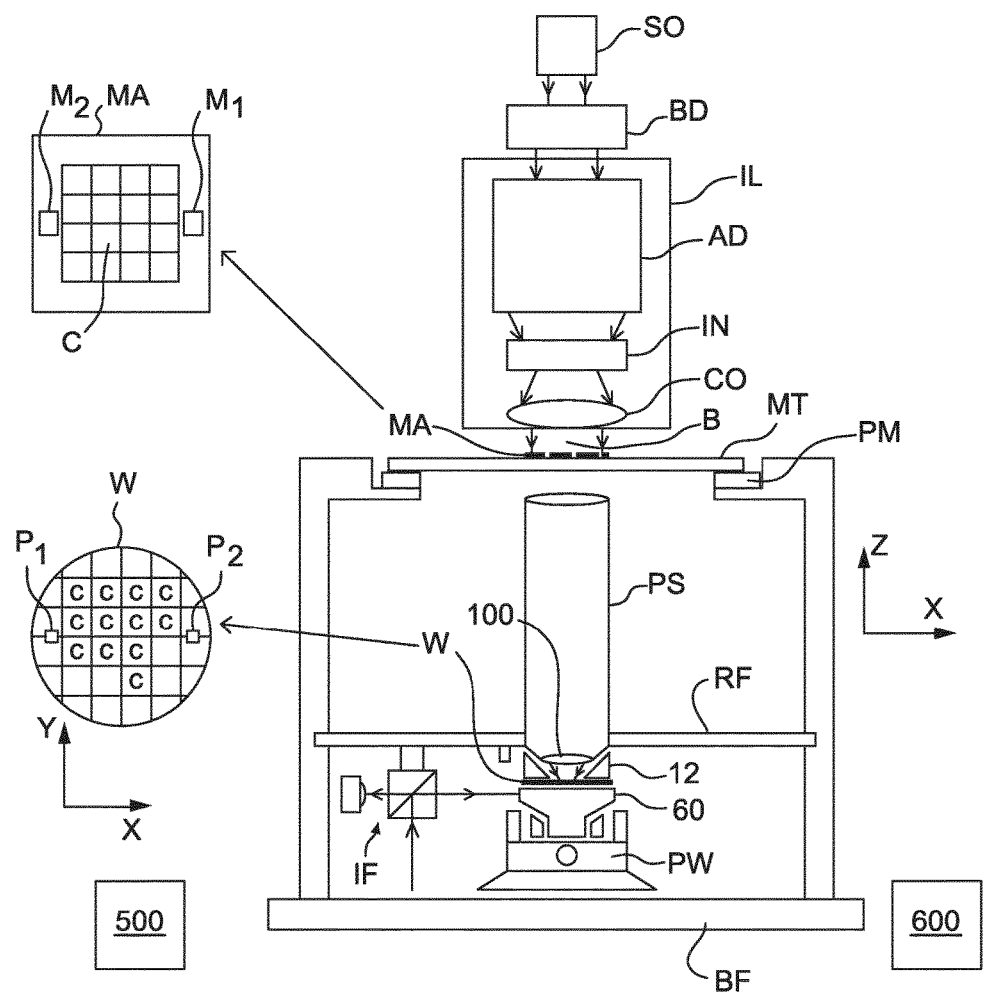
FIG. 1 schematically depicts a lithographic apparatus.

FIG. 1 schematically depicts a lithographic apparatus in which an embodiment of the invention can be used. The apparatus includes an illumination system (illuminator) IL configured to condition a radiation beam B (e.g. UV radiation or any other suitable radiation), a mask support structure (e.g. a mask table) MT constructed to support a patterning device (e.g. a mask) MA and connected to a first positioning device PM configured to accurately position the patterning device in accordance with certain parameters. The apparatus also includes a substrate table (e.g. a wafer table) WT or "substrate support" constructed to hold a substrate (e.g. a resist coated wafer) W and connected to a second positioning device PW configured to accurately position the substrate in accordance with certain parameters. The apparatus further includes a projection system (e.g. a refractive projection lens system) PS configured to project a pattern imparted to the radiation beam B by patterning device MA onto a target portion C (e.g. including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The mask support structure supports, i.e. bears the weight of, the patterning device. It holds the patterning device in a manner that depends on the orientation of the patterning device, the design of the lithographic apparatus, and other conditions, such as for example whether or not the patterning device is held in a vacuum environment. The mask support structure can use mechanical, vacuum, electrostatic or other clamping techniques to hold the patterning device. The mask support structure may be a frame or a table, for example, which may be fixed or movable as required. The mask support structure may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section so as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam which is reflected by the mirror matrix.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

As here depicted, the apparatus is of a transmissive type (e.g. employing a transmissive mask). Alternatively, the apparatus may be of a reflective type (e.g. employing a programmable mirror array of a type as referred to above, or employing a reflective mask).

The lithographic apparatus may be of a type having two (dual stage) or more substrate tables or "substrate supports" (and/or two or more mask tables or "mask supports"). In such "multiple stage" machines the additional tables or supports may be used in parallel, or preparatory steps may be carried out on one or more tables or supports while one or more other tables or supports are being used for exposure.

The lithographic apparatus may also be of a type wherein at least a portion of the substrate may be covered by a liquid having a relatively high refractive index, e.g. water, so as to fill a space between the projection system and the substrate. An immersion liquid may also be applied to other spaces in the lithographic apparatus, for example, between the mask and the projection system. Immersion techniques can be used to increase the numerical aperture of projection systems. The term "immersion" as used herein does not mean that a structure, such as a substrate, must be submerged in liquid, but rather only means that a liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD configured to adjust the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask MA), which is held on the mask support structure (e.g., mask table MT), and is patterned by the patterning device. Having traversed the mask MA, the radiation beam B passes through the projection system PS, which focuses the beam onto a target portion C of the substrate W. With the aid of the second positioning device PW and position sensor IF (e.g. an interferometric device, linear encoder or capacitive sensor), the substrate table WT can be moved accurately, e.g. so as to position different target portions C in the path of the radiation beam B. Similarly, the first positioning device PM and another position sensor (which is not explicitly depicted in FIG. 1) can be used to accurately position the mask MA with respect to the path of the radiation beam B, e.g. after mechanical retrieval from a mask library, or during a scan.

In general, movement of the mask table MT may be realized with the aid of a long-stroke module (coarse positioning) and a short-stroke module (fine positioning), which form part of the first positioning device PM. Similarly, movement of the substrate table WT or "substrate support" may be realized using a long-stroke module and a short-stroke module, which form part of the second positioner PW. In the case of a stepper (as opposed to a scanner) the mask table MT may be connected to a short-stroke actuator only, or may be fixed. Mask MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the mask MA, the mask alignment marks may be located between the dies.

A controller 500 controls the overall operations of the lithographic apparatus and in particular performs an operation process described further below. Controller 500 can be embodied as a suitably-programmed general purpose computer comprising a central processing unit, volatile and non-volatile storage means, one or more input and output devices such as a keyboard and screen, one or more network connections and one or more interfaces to the various parts of the lithographic apparatus. It will be appreciated that a one-to-one relationship between controlling computer and lithographic apparatus is not necessary. One computer can control multiple lithographic apparatuses. Multiple networked computers can be used to control one lithographic apparatus. The controller 500 may also be configured to control one or more associated process devices and substrate handling devices in a lithocell or cluster of which the lithographic apparatus forms a part. The controller 500 can also be configured to be subordinate to a supervisory control system of a lithocell or cluster and/or an overall control system of a fab.

A download station 600, described further below, is provided as part of the lithographic apparatus or as a separate device elsewhere in the fab, perhaps close to the lithographic apparatus or at a central location. The download station is connected to controller 500, a supervisory control system and/or the overall control system. The download station can incorporate a computer system programmed to analyze the information obtained from the inspection substrate, or such analysis can be performed elsewhere.

Arrangements for providing liquid between a final lens element of the projection system PS and the substrate can be classed into three general categories. These are the bath type arrangement, the so-called localized immersion systems and the all-wet immersion systems. The present invention relates particularly to the localized immersion systems.

In an arrangement which has been proposed for a localized immersion system, a liquid confinement structure 12 extends along at least a part of a boundary of an immersion space between the final lens element of the projection system PS and the facing surface of the stage or table facing the projection system. The facing surface of the table is referred to as such because the table is moved during use and is rarely stationary. Generally, the facing surface of the table is a surface of a substrate W, substrate table WT which surrounds the substrate or both.

In an embodiment, the liquid confinement structure 12 as illustrated in FIG. 1 may extend along at least a part of a boundary of the immersion space between the final lens element 100 of the projection system PS and the substrate table WT or substrate W. In an embodiment, a seal is formed between the liquid confinement structure 12 and the surface of the substrate W/substrate table WT. The seal may be a contactless seal such as a gas seal (such a system with a gas seal is disclosed in European patent application publication no. EP-A-1,420,298) or a liquid seal.

The liquid confinement structure 12 is configured to supply and confine immersion liquid to the immersion space. Liquid may be brought into the immersion space by a liquid inlet and the liquid may be removed by a liquid outlet.

The liquid may be contained in the immersion space by a gas seal which, during use, is formed between the bottom of the liquid confinement structure 12 and the facing surface of the table (i.e. the surface of the substrate W and/or the surface of the substrate table WT). The gas in the gas seal is provided under pressure via an inlet to a gap between the liquid confinement structure 12 and substrate W and/or substrate table WT. The gas is extracted via a channel associated with an outlet. The overpressure on the gas inlet, vacuum level on the outlet and geometry of the gap are arranged so that there is a high-velocity gas flow inwardly that confines the liquid. The force of the gas on the liquid between the liquid confinement structure 12 and the substrate W and/or substrate table WT contains the liquid in the immersion space 10. Such a system is disclosed in United States patent application publication no. US 2004-0207824. Other liquid confinement systems 12 can be used with the present invention.

Figure 2:
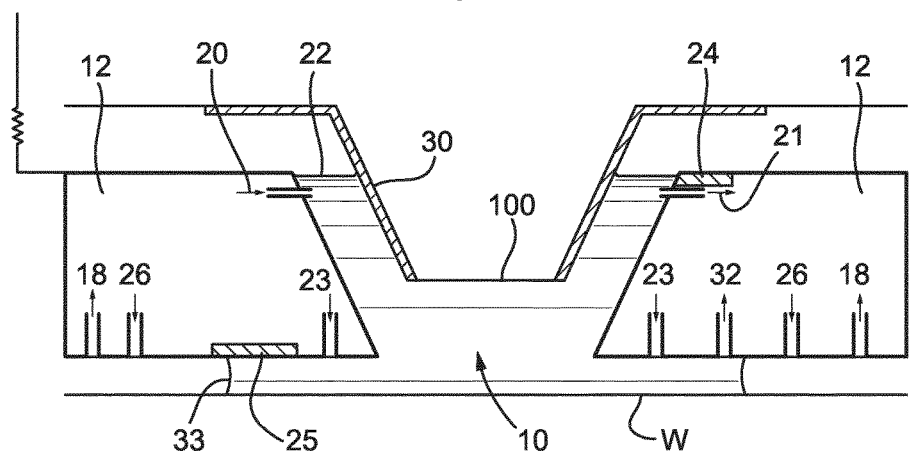
FIG. 2 schematically depicts two immersion liquid confinement structure arrangements for use in a lithographic projection apparatus.
Figure 3:
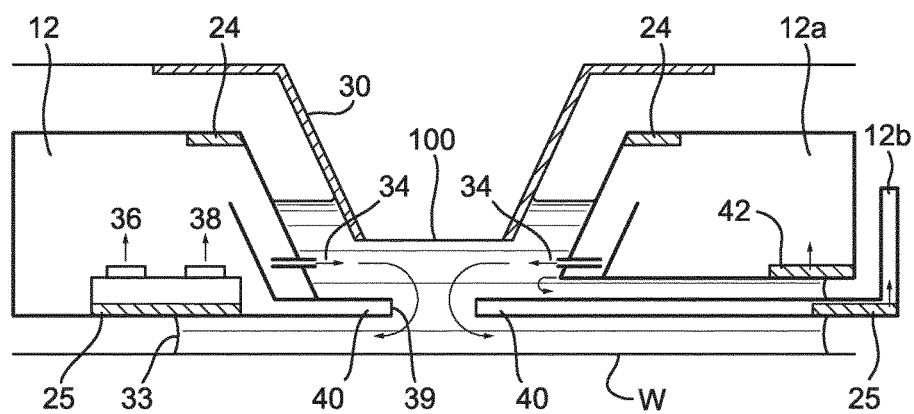
FIG. 3 is a side cross sectional view that schematically depicts two further immersion liquid confinement structure arrangements according to an embodiment.

FIGS. 2 and 3 show different features which may be present in variations of the liquid confinement structure 12. The arrangements illustrated in FIG. 2 and described below may be applied to the lithographic apparatus described above and illustrated in FIG. 1. The two different arrangements are shown for features on the bottom left-hand-side and bottom right-hand side of the figure, respectively. Unless mentioned otherwise, the two designs share common features. The designs may share some of the same features as described above unless described differently. The features described herein may be selected individually or in combination as shown or as required.

FIG. 2 shows a confinement structure 12 around the bottom surface of a last lens element. The last lens element 100 has an inverted frustro-conical shape. The frustro-conical shape having a planar bottom surface and a conical surface. The frustro-conical shape protrudes from a planar surface and having a bottom planar surface. The bottom planar surface is the optically active portion of the bottom surface of the last lens element, through which the projection beam may pass. The confinement structure surrounds at least part of the frustro-conical shape. The confinement structure has an inner-surface which faces towards the conical surface of the frustro-conical shape. The inner-surface and the conical surface have complementary shape. A top surface of the confinement structure is substantially planar. The confinement structure may fit around the frustro-conical shape of the last lens element. A bottom surface of the liquid confinement structure is substantially planar and in use the bottom surface may be parallel with the facing surface of the table and/or wafer. The distance between the bottom surface and the facing surface may be in the range of 30 to 500 micrometers, desirably in the range of 80 to 200 micrometers.

The liquid confinement structure 12 extends closer to the facing surface of the wafer W and wafer table WT than the last lens element 100. An immersion space 10 is therefore defined between the inner surface of the liquid confinement structure 12, the planar surface of the frustro-conical portion and the facing surface. During use, the immersion space 10 is filled with liquid. The liquid fills at least part of a buffer space between the complementary surfaces between lens and the liquid confinement structure 12, in an embodiment at least part of the immersion space 10 between the complementary inner-surface and the conical surface.

Liquid is supplied to the immersion space 10 through an opening formed in the surface of the liquid confinement structure 12. The liquid may be supplied through a supply opening 20 in the inner-surface of the liquid confinement structure. Alternatively or additionally, the liquid is supplied from an under supply opening 23 formed in the undersurface of the liquid confinement structure 12. The under supply opening may surround the path of the projection beam and it may be formed of a series of openings in an array. The liquid is supplied to fill the immersion space 10 so that flow through the space under the projection system is laminar. The supply of liquid from the under supply opening 23 under the liquid confinement structure 12 additionally prevents the ingress of bubbles into the immersion space 10. This supply of liquid functions as a liquid seal.

The liquid may be recovered from a recovery opening 21 formed in the inner-surface. The recovery of the liquid through the recovery opening 21 may be by application of an under pressure; the recovery through the recovery opening 21 as a consequence of the velocity of the liquid flow through the space; or the recovery may be as a consequence of both. The recovery opening 21 may be located on the opposite side of the supply opening 20, when viewed in plan. Additionally or alternatively, the liquid may be recovered through an overflow opening 24 located on the top surface of the liquid confinement structure 12, as shown in the right-hand arrangement. Note that if present the overflow may extend around the top of the liquid confinement structure, around the path of the projection beam.

Additionally or alternatively, liquid may be recovered from under the liquid confinement structure 12 through a bottom recovery opening 25, 32. A meniscus 33 forms between the liquid confinement structure 12 and the facing surface and it serves as border between the liquid space and the gaseous external environment. The bottom recovery opening may be a porous plate 25 which may recover the liquid in a single phase flow. The meniscus may be free to move over the surface of the porous plate during relative movement of facing surface relative to the liquid confinement structure. Alternatively, the bottom recovery opening 25, may serve to hold (or 'pin') the liquid meniscus 33 to the liquid confinement structure 12. The bottom recovery opening may be a series of pinning openings 32 through which the liquid is recovered. The pinning openings 32 may recover the liquid in a two phase flow.

Optionally radially outward, with respect to the inner-surface of the liquid confinement structure 12, is an gas knife opening 26. Gas may be supplied through the gas knife opening 26 at elevated speed to assist confinement of the immersion liquid in the immersion space 10. The supplied gas may be humidified and it may contain carbon dioxide. The supplied gas may consist essentially of carbon dioxide and water vapor. Radially outward of the gas knife opening 26 is a gas recovery opening 18 for recovering the gas supplied through the gas knife opening 26.

FIG. 3 depicts two further arrangements of liquid confinement structure 12. The two different arrangements are shown for features on the bottom left-hand-side and bottom right-hand side of the figure, respectively. Unless mentioned otherwise, the two designs share common features. Features of the two arrangements shown in FIG. 3 which are common to FIG. 2 share the same reference numbers. The liquid confinement structure 12 has an inner surface which complements the conical surface of the frustro-conical shape. The undersurface of the liquid confinement structure 12 is closer to the facing surface than the bottom planar surface of the frustro-conical shape.

Liquid is supplied to the immersion space 10 through supply openings formed in the inner surface of the liquid confinement structure 12. The supply openings 34 are located towards the bottom of the inner surface, perhaps below the bottom surface of the fustro-conical shape. The supply openings 34 are located on an inner surface, spaced apart around the path of the projection beam.

Liquid is recovered from the immersion space 10 through recovery openings 25 in the undersurface of the liquid confinement structure 12. As the facing surface moves under the liquid confinement structure 12, the meniscus 33 may migrate over the surface of the recovery opening 25 in the same direction as the movement of the facing surface. The recovery openings 25 may be formed of a porous member. The liquid may be recovered in single phase flow. In an embodiment the liquid is recovered in a two phase flow. The two phase flow is received in a chamber 35 within the liquid confinement structure 12 where it is separated into liquid and gas. The liquid and gas are recovered through separate channels 36, 38 from the chamber 35.

An inner periphery 39 of the undersurface of the liquid confinement structure 12 extends into the space away from the inner surface to form a plate 40. The inner periphery forms a small aperture which may be sized to match the shape and size of the projection beam. The plate may serve to isolate liquid either side of it. The supplied liquid flows inwards towards the aperture, through the inner aperture and then under the plate radially outwardly towards the surrounding recovery openings 25.

In an embodiment the liquid confinement structure 12 may be in two parts: an inner part 12a and an outer part 12b. For convenience this arrangement is shown in the right-hand part of FIG. 3. The two parts may move relatively to each other, in a plane parallel to facing surface. The inner part may have the supply openings 34 and it may have the overflow recovery 24. The outer part 12b may have the plate 40 and the recovery opening 25. The inner part may have an intermediate recovery 42 for recovering liquid which flows between the two parts.

Contamination of various types can adversely affect the performance of a fluid handling system in a lithographic apparatus. Although the environment of the lithographic apparatus is kept to a very low contaminant level and the immersion liquid, e.g. water, is very pure, the possibility of particulate contamination of the fluid handling system cannot be wholly eradicated. The presence of even small contaminants at critical locations within the fluid handling system can reduce its effectiveness. For example, the presence of a fiber on, for example adhered to, the lower surface of a liquid confinement structure 12 may increase defectivity and may contribute to a reduction in productivity. The presence of a fiber adjacent, or even over, a water extraction orifice can lead to additional water loss onto a production substrate during exposures. Also, a partial or complete blockage of a gas outlet forming part of a gas seal for confining the immersion liquid can lead to water loss onto a production substrate. Water loss on a production substrate can cause defects in exposed patterns. The defects may be formed through the creation of watermarks on the resist as a consequence of evaporating droplets. In a different mechanism, a bubble may be generated on collision between the meniscus of the confined immersion liquid and a droplet remaining on the substrate. The bubble may travel in the immersion space to interfere with the path of the projection beam.

It is often difficult to detect that contamination has reduced the effectiveness of the liquid confinement system. Often the first sign of contamination of a confinement structure 12 will be a decrease in yield due to an increase in the number of defects in exposed patterns; the risk of an increase in defect count may not become immediately apparent. Opening the lithographic apparatus to inspect the liquid confinement structure for contaminants is time consuming. The procedure of inspection presents a risk of contamination, so it is undesirable to perform such an inspection unless absolutely necessary.

The present invention proposes an inspection substrate that can be loaded into the lithographic apparatus as if it were a production substrate to be exposed. The inspection substrate is interchangeable with a production substrate. The inspection substrate is compatible with the lithographic apparatus. The inspection substrate contains one or more sensors that are configured to inspect a component, or a parameter of a component, of the lithographic apparatus. During inspection, which may be during operation of the lithographic apparatus, the inspection substrate is adjacent, or proximate to the component. With respect to the inspection substrate, the component may be detectable from the path through the apparatus of a normal with respect to the upper surface of a production substrate (and therefore the inspection substrate). The component may be a functional subsystem of the lithographic apparatus such as a liquid confinement system or a part of a functional subsystem.

The inspection substrate of the present invention contains sensors, such as electronic sensors, which make measurements of a parameter of component. Parameters which can be measured include: surface topology, contamination or damage, which may be measured by imaging. Other parameters include operational status, e.g. measured by detecting a pressure generated by the operation of the component, and temperature. The measurements are then stored in memory integrated into the inspection substrate. It should therefore be contrasted with a test substrate on which test exposures are carried out in order to characterize the performance of the lithographic apparatus. (Such a test substrate may be referred to as a 'witness substrate' in that the substrate takes the place of an exposure substrate for testing purposes. The witness substrate may be coated with typical substrate coatings, such as photosensitive resist, so that tests which may involve test exposures may be carried out to gain information regarding the processes applied to exposure substrates; as if the witness substrate was an exposure substrate).

The sensors of the inspection substrate of the present invention make a local measurement, e.g. with a range of less than 1 to 10 mm. Sensing substrates with integrated image sensors for detecting the projection beam are known but are only capable of measuring the projection beam and not other functional subsystems. Since the inspection substrate of the present invention does not measure the projection beam it need not be capable of withstanding DUV radiation. In the absence of exposure to DUV exposure light, the risks to DUV radiation on the lifetime on the inspection substrate are minimal. An inspection substrate according to an embodiment of the present invention is particularly useful in inspecting a liquid confinement system, especially a liquid confinement structure. A feature of the liquid confinement structure which the inspection substrate may be used to inspect is the undersurface of the liquid confinement structure. Inspection of features present in the undersurface such as the openings for the passage of liquid and gas can be achieved using the inspection substrate of the present invention.

Figure 4:
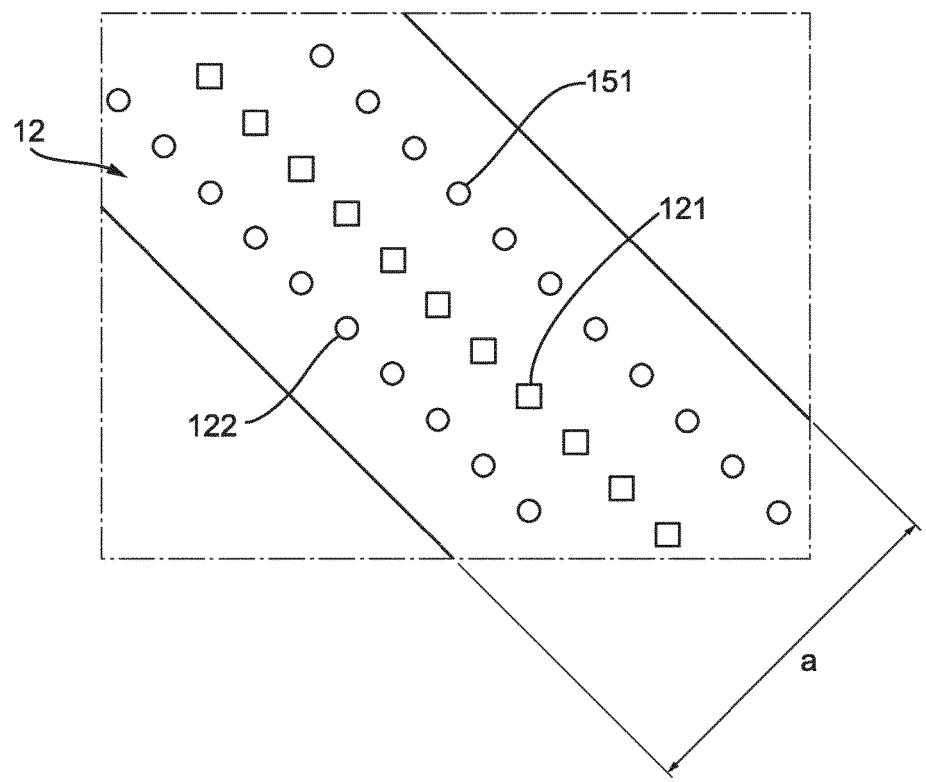
FIG. 4 depicts the underside of a part of an immersion liquid confinement structure for use in a lithographic projection apparatus.

FIG. 4 depicts the underside of a liquid confinement structure 12 in a lithographic apparatus. The lower surface of the liquid confinement structure 12, that is the surface which faces the substrate W during operation of the lithographic apparatus, is provided with several generally parallel rows of apertures. The rows arranged may be generally arranged concentrically around the immersion space. As described with reference to FIGS. 2 and 3, they may be used to help confine the immersion liquid to the immersion space 10. These apertures may include (in a non-limited list) gas seal apertures 151, liquid extraction apertures 121 and liquid supply apertures 122. The gas seal apertures 151 are supplied, when operating, with gas at a high pressure so as to form a high pressure region between the liquid confinement structure 12 and substrate W. The high pressure region functions to confine the immersion liquid to the immersion space 10 and is referred to as a gas seal. The liquid extraction apertures 121 are connected to a low pressure source and in use extract gas and/or immersion liquid in a one or two phase flow. The liquid extraction apertures 121 can function as a meniscus pinning feature. Liquid supply apertures 122 supply liquid to the immersion space, e.g. to replenish liquid removed through the liquid extraction apertures 121.

The total width a of the inspected object, e.g. liquid confinement structure 12, may be of the order of 4 to 40 mm, or larger. The various apertures described may have different sizes, e.g. of the order of 10 µm to 1 mm. Therefore, a small contaminant particle can easily block or disrupt the flow around any of the apertures. If the contaminant is a fiber, a single fiber could obstruct one or more openings along a row of openings. Detecting a contaminant particle therefore may require microscopic inspection of the liquid confinement structure 12 which can be very time-consuming. It is often necessary to inspect the whole of the liquid confinement structure 12 undersurface if contamination is suspected since available information does not provide precise diagnostic information. For example a higher of count of defects per wafer than expected might well not give any clue as to the number or locations of any contaminants on the liquid confinement structure.

Figure 5:
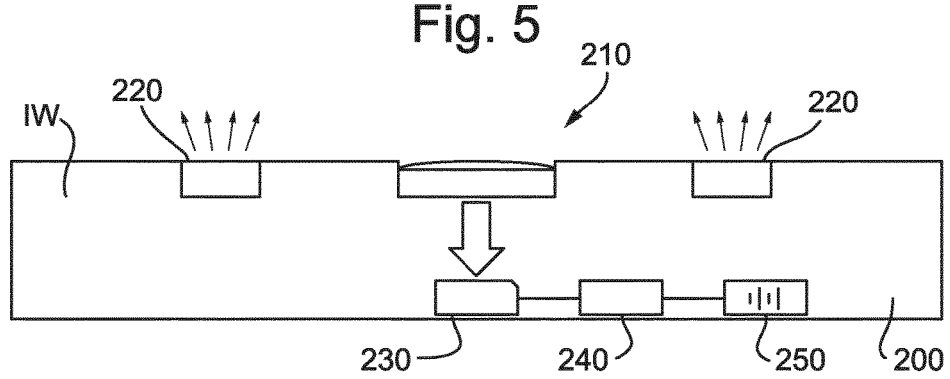
FIG. 5 depicts an inspection substrate according to an embodiment of the invention.

FIG. 5 depicts an inspection substrate IW according to an embodiment of the present invention. Inspection substrate IW comprises an inspection body that can be loaded into and transported by the lithographic apparatus. The inspection body may be made of the same material as production substrate. The body may have dimensions similar to, or substantially the same as, a production substrate. Therefore, the inspection substrate IW can be loaded into and handled by the lithographic apparatus in the same way as a production substrate. Inspection substrate body 200 may be a silicon wafer, e.g. of diameter 300 mm or 450 mm.

Embedded in inspection substrate body 200 are: an imaging device 210; an illuminating device 220; a storage device 230; a controller and interface 240; and a power storage device 250. These various components of the inspection substrate may be manufactured, e.g. by use of lithographic techniques, directly onto a surface of the inspection substrate body 200. Additionally or alternatively the components can be separately formed and secured (e.g. by bonding or adhering) into place. A separate component can be secured in place in the inspection substrate body 200 in a recess in inspection substrate body 200. Such a recess may be dimensioned to match substantially the dimensions of the secured component. Desirably the various components of inspection substrate IW do not project out of either major surface of inspection substrate body 200. Where such a component projects from a major surface of the inspection substrate body 200, the component projects no more than is acceptable by the lithographic apparatus, for example no more than 40 micrometers or desirably less, for example, no more than 30 micrometers, or preferably 20 micrometers, or preferably 10 micrometers. Preferably, the projection of the component is small enough not to affect substantially the meniscus stability during stage movement, for example, when the projection moves under the liquid confinement structure 12.

In the event that one or more components of the lithographic apparatus are not perfectly flush with an outer surface of inspection substrate body 200, an additional planarization layer (such as a coating) can be provided to the respective outer surface to ensure that the relevant surface matches the flatness specifications required by the lithographic apparatus.

Inspection substrate IW is desirably configured to be sealed against the inflow of the immersion liquid (e.g. waterproof) into the inspection substrate body. Additionally or alternatively, the inspection substrate IW is desirably resistant to immersion liquid. For example, any gaps formed between a component in a recess of the inspection substrate body and the inspection substrate body are effectively sealed. Further, even if such a gap were to form at such a recess, the inspection substrate IW would be sufficiently resistant to the inflow of any liquid into such a gap. For these reasons, the inspection substrate IW can be used with immersion liquid present in the immersion space.

Imaging device 210 can be formed as a standard CMOS or CCD imaging sensor. The sensor may be provided with a microlens. The imaging device 210 is described further below.

Illuminating device 220 can comprise one or more light emitting diodes or laser diodes. In an embodiment, illuminating device 220 comprises a plurality of white light emitting diodes—e.g. four, six or eight—disposed around imaging device 210. Illuminating device 220 may be configured to emit radiation of any convenient wavelength, e.g. in the infrared, ultraviolet or visible ranges. Illuminating device 220 desirably emits radiation that can be detected by imaging device 210 so that a phosphorescent or scintillation layer is not required. Illuminating device 220 may be configured to emit radiation of a wavelength or wavelengths in which expected forms of contamination contrast most strongly with the material of the object to be inspected. Desirably the radiation has a wavelength shorter than the diameters of contaminant particles to be detected. Illuminating device 220 can be configured to emit radiation of a polarization state in which the expected forms of contamination contrast most strongly with the material of the object to be inspected. Illuminating device 220 can be configured to provide dark field illumination, i.e. the direction of illumination is selected so that specularly reflected radiation does not reach the imaging device 210. Illuminating device 220 may be provided with multiple illumination elements that emit different wavelengths or polarization states and are separately controllable so as to allow images to be taken under different illumination conditions.

Storage device 230 desirably takes the form of non-volatile memory such as NAND flash memory. However, static or dynamic RAM may be used if power storage device 250 is capable of providing sufficient power for long enough for the inspection substrate IW to be removed from the lithographic apparatus and data downloaded.

Controller and interface 240 controls the overall operations of the inspection substrate IW. The controller and interface 240 communicates with external devices. Controller and interface 240 may comprise a microprocessor, program memory and working memory. Additionally or alternatively, controller and interface 240 may use a section of storage device 230 to store a program to be executed and for making memory. Controller and interface 240 may be configured to communicate with different components of the inspection substrate and externally to the inspection substrate IW, using a wired protocol (e.g. USB or IEEE 1394), or a wireless protocol (e.g. Wi-Fi™ or Bluetooth™), or both. In view of high levels of electromagnetic noise often present in a lithographic apparatus wireless communication with the inspection substrate might only be effective when the inspection substrate is outside the lithographic apparatus.

Power storage device 250 may be a battery. The device 250 is desirably a secondary cell, such as a lithium-ion cell. Additionally or alternatively power storage device 250 can be a supercapacitor.

Figure 6:
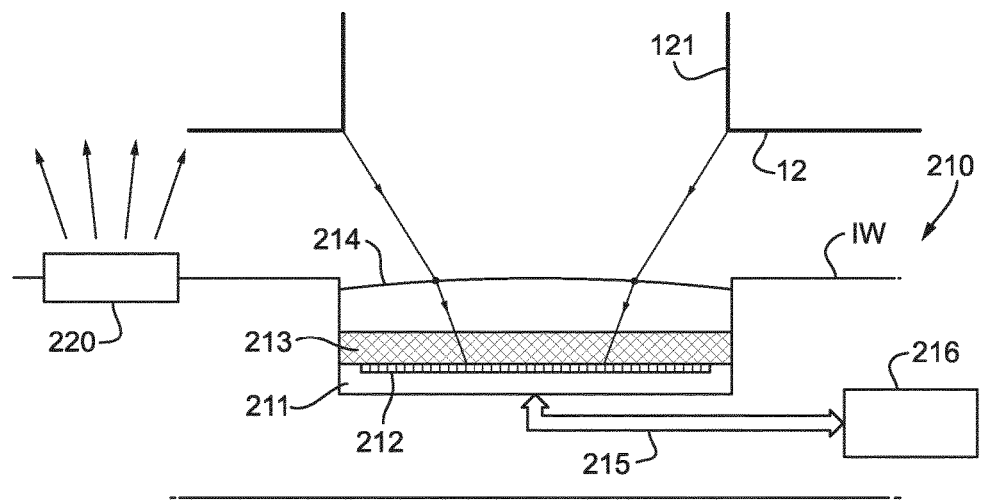
FIG. 6 depicts in cross section a part of an inspection substrate according to an embodiment of the present invention.

FIG. 6 depicts in cross section a part of the inspection substrate IW in use to image a lower surface of immersion liquid confinement structure 12. Imaging device 210 comprises an image sensor 211 that includes a two-dimensional array of imaging elements 212. Above the two-dimensional array of imaging elements 212 is provided a filler layer 213, which may include a spectral filter and/or a polarizing filter. A polarizing filter can increase the contrast between diffuse reflections and specular reflections. In the event that imaging device 210 is a color imaging device, the spectral filter may be a Bayer filter array. Above filler layer 213 is provided microlens 214. Microlens 214 is configured to form an image of the lower surface of a part of the lower surface immersion liquid confinement structure 12 onto at least a part of the two-dimensional array of image sensing elements 212. The inspection substrate IW may be substantially flat or planar. However, the microlens 214 may desirably have a curved upper surface (as depicted in FIG. 6) to enable better functionality, but this may not always be the case. The curvature of microlens 214 is significantly exaggerated in this figure.

In an embodiment, imaging device is not parallel to the surface of the inspected object and an optical element—e.g. an optical wedge, prism or folding mirror—is provided to appropriately direct the image onto the imaging device.

The working distance between inspection substrate IW and the inspected object, e.g. a component of the lithographic apparatus such as the lower surface of liquid confinement structure 12, is short. Because of the short working distance it is difficult to form an image of a large area, or surface, of the inspected object using just a single microlens. If the area that can be imaged at one time is insufficient, it is possible to enable imaging of a larger area of the inspected object for example by taking multiple images whilst moving the inspection substrate IW short distances (i.e. shifting the substrate stage WT that holds the inspection substrate IW) between images. Other techniques to increase the effective size of the area that can be imaged exist and some of them are described here. Some of them enable the size of the area imaged in one image to be increased. In an embodiment the inspected object, e.g. the lower surface of the liquid confinement structure, may be moved from its normal position, e.g. raising the liquid confinement surface, to increase the working distance between the inspection substrate IW and the lower surface of the liquid confinement structure. Raising the liquid confinement structure enables a greater area of the surface of the lower surface of the liquid confinement structure to be imaged.

In an embodiment of the present invention, it may only be necessary to inspect a small part of the component and therefore the field of view of imaging device 210 on the component, e.g. lower surface of liquid confinement structure 12, can be less than about 5 mm2, e.g. less than 1 mm2, e.g. about 0.4 mm×0.4 mm. The focal length of microlens 214 is less than about 5 mm, e.g. less than 1 mm. Microlens 214 may be a Fresnel lens in order to provide a greater optical power in a given thickness or to reduce the thickness of the lens for a given optical power.

In an embodiment, the image of the part of liquid confinement structure 12 is projected onto an array of pixels in the two-dimensional array of image sensing elements 212. The size of the array depends on the desired imaging resolution and the desired field of view. Commercially available designs of image sensor provide sufficient numbers of pixels to provide both ample resolution and field of view. Desirably the imaging device is capable of resolving features on the object to be inspected of dimensions less than 100 μm, more desirably less than 10 μm, for example about 1 μm. If imaging device 210 is a monochrome imaging device, then each pixel may correspond to a single image sensing element. If imaging device is a color imaging device then each pixel may correspond to a group of four image sensing elements. Imaging device 210 further comprises a bus 215 connecting it to readout circuit 216. The readout circuit 216 controls the readout process and performs pre-amplification on the output signals which are then communicated to storage device 230. Even if only a part of the array of imaging elements 212 is used, it may be economical to use a commercially available imaging device 210 that is larger than necessary rather than a custom designed device. This is because existing commercial masks and processes can be used to form the imaging device 210. Additional expense in developing a new design and custom masks can be avoided.

Figure 7:
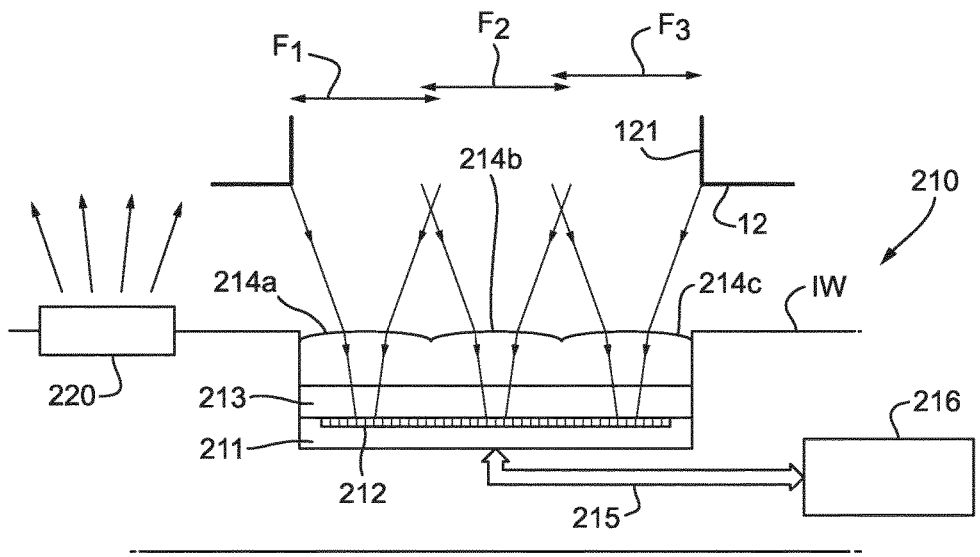
FIG. 7 depicts in cross section a part of an inspection substrate according to an embodiment of the present invention.

FIG. 7 depicts a variant of image sensing device 210 in which microlens 214 is formed into several lens sections 214a, 214b, 214c. Desirably the fields of view of the lens sections abut or overlap so as to form a contiguous image of a portion of the surface of the inspected object, such as the lower surface of the liquid confinement structure 12. This arrangement of multiple lenses with overlapping fields of view enables a larger portion of the inspected surface than is possible using a single microlens 214 as depicted in FIG. 6.

Figure 8:
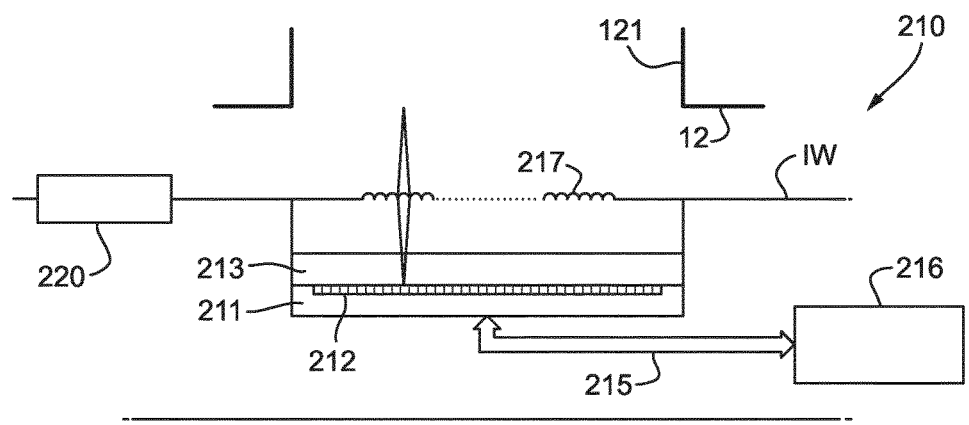
FIG. 8 depicts in cross section a part of an inspection substrate according to an embodiment of the present invention.

FIG. 8 depicts a further variant of imaging device 210. The depicted imaging device 210 has a microlens array 217 comprising a plurality of microlenses in one-to-one relationship with a plurality of image sensing elements. The image sensing elements are in a two-dimensional array of image sensor elements 212. This arrangement is especially suitable when the working distance between imaging device 210 and the object to be inspected is very small.

In an embodiment of the invention, inspection substrate IW is provided with a plurality of imaging devices 210 so as to enable the object to be inspected to be scanned more quickly. The arrangement of imaging devices 210 on inspection substrate IW can be optimized to at least a part of the shape of the object to be imaged so as to most efficiently image it. If the imaging devices 210 form a pattern which matches the shape of the inspected object, then the imaging of the inspected object can be taken one image. If the pattern formed by the imaging devices formed on the inspection substrate IW corresponds to a part of a shape of the inspected object, a number of images would be made before the inspection of the inspected object is complete. For example if the imaging devices form a pattern corresponding to a side of a four sided shape formed by the openings in the underside of the liquid confinement structure, four images should be made before inspection of the confinement structure undersurface is completed. The number of imaging devices 210 may be further minimized if the inspection substrate IW is moved whilst the imaging process is carried out. If a liquid confinement structure having a different shape, e.g. round or oval, a different arrangement of imaging devices can be used. If it is only desired to inspect a part of a liquid confinement structure, e.g. an opening or array of openings for fluid, the number and arrangement of the imaging devices can be adapted to the shape of the part that is to be inspected rather than the whole liquid confinement structure.

Figure 9:
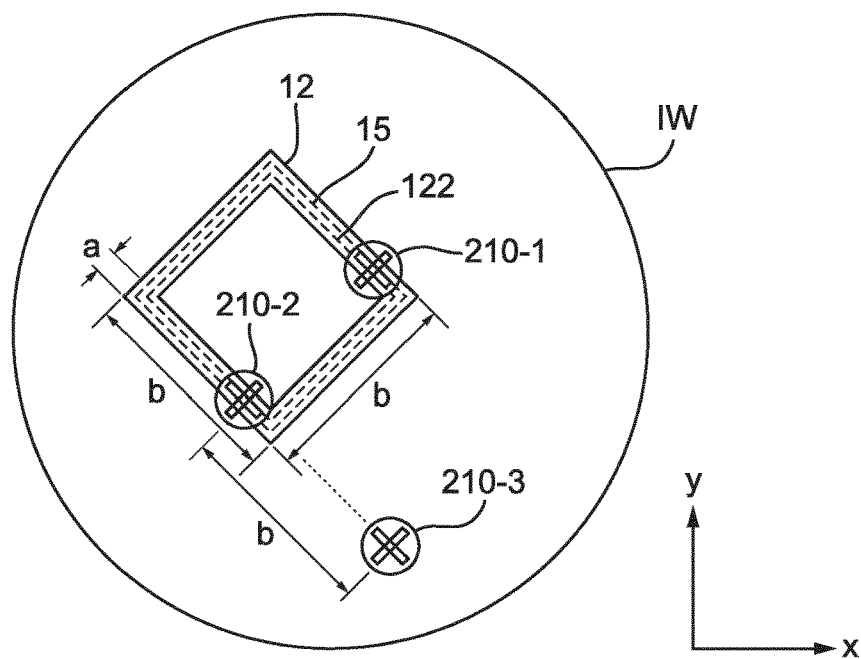
FIG. 9 depicts an inspection substrate according to an embodiment of the present invention.

For example, in an embodiment of inspection substrate IW to image the complete lower surface of a liquid confinement structure 12 that has the shape in plan of a square frame oriented at 45° to x and y axes of the apparatus, an arrangement of image sensing devices 210 as shown in FIG. 9 can be used. This arrangement comprises three image sensing elements 210 each having a field of view having a dimension at least equal to the width of one side of the liquid confinement structure 12, or more specifically, or in the alternative, the width of a row of openings forming a pattern on the underside of the liquid confinement structure 12. The image sensing devices 210-1, 210-2 and 210-3 are spaced apart by a distance b equal to the length of one side of the liquid confinement structure. The length 'b' may more specifically, or in the alternative, be the separation between centers of the sides of the liquid confinement structure 12. In use, the inspection substrate IW is orientated in the lithographic apparatus such that the two of the imaging devices, e.g. 210-1, 210-2 can be located under a pair of adjoining corners of the shaped formed by the rows of opening in the undersurface of the liquid confinement structure 12. Thus, an imaginary line joining two of the imaging devices, e.g. 210-1 and 210-2, is parallel to one side (e.g. a first side) of the liquid confinement structure 12.

In the same orientation of the inspection substrate IW relative to the lithographic apparatus another pair of the imaging devices, e.g. 210-2, 210-3 can be located under another pair of adjoining corners of the shaped formed by the rows of opening in the undersurface of the liquid confinement structure 12. Thus, an imaginary line joining another two of the imaging devices, e.g. imaging devices 210-2 and 210-3, is parallel to another side (e.g. a second side) of liquid confinement structure 12. The first and second sides may be adjoining sides of the shape in the undersurface of the liquid confinement structure 12.

With such an arrangement and a liquid confinement structure of that shape, two opposite sides of liquid confinement structure 12 can be scanned simultaneously with one movement of imaging wafer IW relative to liquid confinement structure 12. The other two opposing sides of liquid confinement structure 12 can then be imaged with a single further scan of inspection substrate IW relative to liquid confinement structure 12.

Additional image sensing devices 210-n maybe located on the inspection substrate IW. The additional image sensing devices 210-n may be spaced apart by a distance equal to a fraction of the distance b along imaginary lines parallel to the sides of the liquid confinement structure 12. Having additional image sensing devices 210-n can allow a whole side of the liquid confinement structure 12 to be imaged in a shorter scan.

Figure 10:
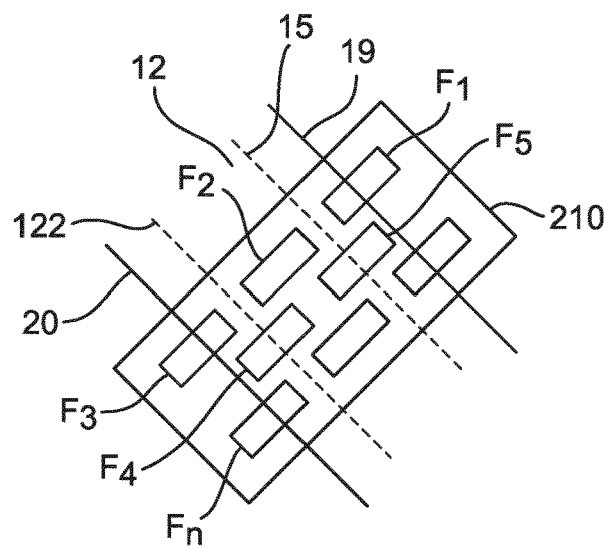
FIG. 10 depicts an arrangement of fields of view of an imaging device of an embodiment of the present invention.

The separation between the imaged object and the image sensor can be too small to allow a complete width of the area to be imaged to be formed as a single image on the image sensor 210. In that event the microlens 214 can be arranged to form a staggered array of images of smaller parts of the imaged object as shown in FIG. 10. After scanning, the collected images can be processed to generate a single contiguous image of the desired object.

As shown in FIG. 10 the microlens 214 of the image sensing device 210 is arranged in a two dimension array of elements, F1 to Fn. In the figure an arrangement of microlens elements are shown in a formation of two staggered parallel rows; although any staggered formation pattern may have any number of rows which may be parallel. In the shown staggered formation microlens elements F1, F2 and F3 are arranged in a first linear array, spaced apart so that there is a gap in the first linear array between adjoining microlens elements F1, F2 and F3. Microlens elements F4 and F5 are in a second linear array spaced apart from the first linear array. In the second linear array, the microlens elements F4 and F5 are spaced apart from each with a similar spacing between adjoining micro lens elements as the microlens elements F1, F2 and F3. The first and second linear arrays may be substantially straight and may be substantially parallel. The first and second linear arrays differ in that the microlens elements of the second linear array are aligned with the gaps of the first linear array. Therefore, a microlens element of at least one of the first and second linear arrays is intersected in a direction orthogonal to the alignment of the first and second linear arrays.

A third linear array of microlens elements Fn may be spaced apart from the second linear array. The third linear array may take the formation of the first linear array. Although FIG. 10 does not show a fourth linear array, if a fourth linear array is present it would take the formation of the second linear array. Thus successive linear arrays of microlens elements take the staggered formation of the first and second linear arrays.

FIG. 10 also depicts features of the undersurface of the liquid confinement structure 12: an outer edge 19 of the undersurface of the liquid confinement structure, a linear array of gas openings 15, and a linear array of liquid supply openings 122. Although these features of a liquid confinement structure are explicitly depicted, they are intended to correspond to any features, such as openings, present in the surface of the inspected object. Note that the outer edge 19 and an inner limit 20 represent the broadest extent of the detectable features on the inspected object. For example for the shape of the openings in the undersurface of a liquid confinement structure, outer edge 19 and inner limit 20 represent the displacement of radially furthest feature and radially furthest feature, respectively from the path of the projection beam. This may be useful to ensure the full side of the feature of the inspected object is imaged, for example where the side is curved and not straight. See for example the footprint of the liquid confinement structure disclosed in EP 2131241 A2 (which is hereby incorporated by reference in its entirety) which has curved sides.

As shown in FIG. 10, the depicted features 15, 122 are shown in linear arrays aligned at an angle, desirably orthogonal to the linear arrays of the microlens elements. Therefore in moving the imaging substrate in a direction orthogonal to the alignment of the linear arrays enables all the features of the inspected object to be imaged.

Figure 11:
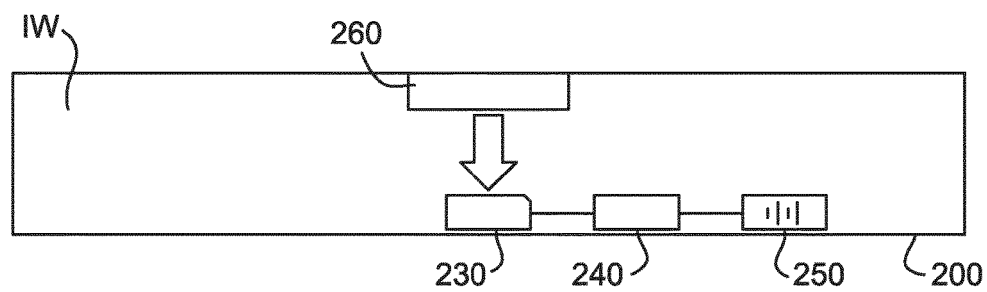
FIG. 11 depicts an inspection substrate according to an embodiment of the present invention.

FIG. 11 depicts an inspection substrate IW' according to another embodiment of the present invention. Inspection substrate IW' is a variant of inspection substrate IW. Parts and components of the further inspection substrate IW' that are the same as the corresponding components of inspection substrate IW are indicated with like reference numerals and are not described further herein for the sake of brevity.

Inspection substrate IW' has a pressure sensor 260 mounted at the upper surface of inspection substrate body 200 so as to measure fluid pressure e.g. gas pressure, immediately adjacent to the upper surface of inspection substrate IW'. Inspection substrate IW' can be used to check for blockages or other malfunctions in the operation of gas seal 16 or liquid supply apertures 122. (Note when checking for blockages of liquid bearing channels and openings, such as liquid supply apertures 122, a gas flow for testing can be sufficient). When operating, gas seal 16 creates a region of high pressure between the liquid confinement structure 12 and a substrate, e.g. a production substrate or inspection substrate IW'. By measuring the pressure underneath gas seal apertures 151 the correct operation of the gas seal can be validated. Inspection substrate IW' can also be used to check for blockages of liquid supply apertures and liquid extraction apparatus in analogous manners.

Figure 12:
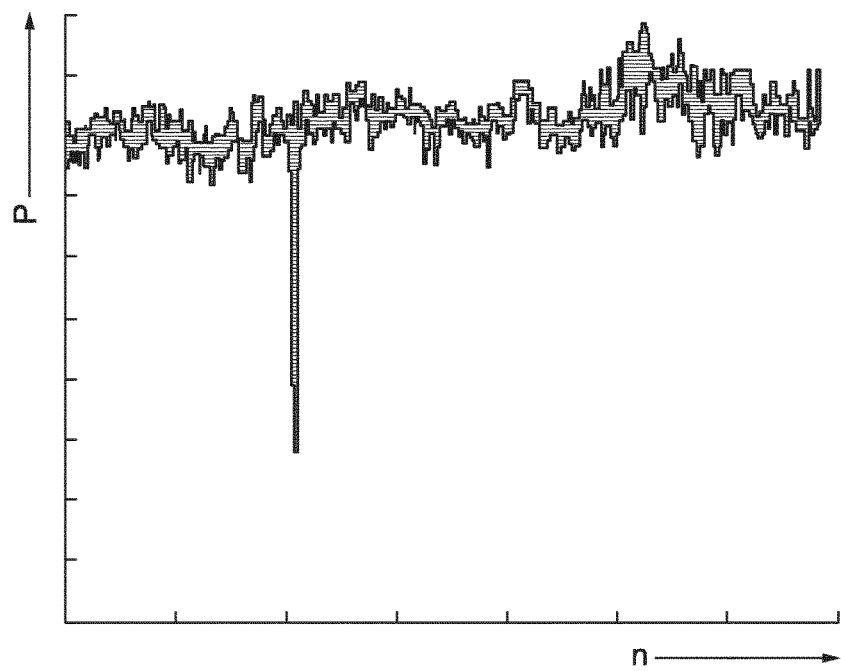
FIG. 12 is a graph showing measured pressure as a function of position using an embodiment of the present invention.

FIG. 12 shows the results of measuring the peak gas pressure P at positions along the line of gas seal apertures 151 opposite each of gas seal apertures 151. The position is indicated by reference to the aperture number n. As can be seen, at most positions the measured pressure fluctuates about a constant, high level, but at one position there is a substantial drop in pressure much greater than the fluctuations at other positions indicating a wholly or partially blocked gas seal aperture 151. The pressure detected in the vicinity of a normally operating gas seal aperture depends on the supply pressure and operating height (sometimes referred to as flight height) of the liquid confinement structure during the measurement process. The supply pressure and operating height need not be the same as are used during production exposures when immersion liquid is present. Experiments by the inventors show that a blocked or partially blocked gas seal aperture causes a pressure drop that is readily distinguishable from pressure fluctuations occurring at the positions of properly operating gas seal apertures. Since during testing, gas flow is used to check any of the performance of any of the sets of openings in the undersurface of the liquid confinement structure, the same technique can be used to test the performance of the other fluid openings.

Pressure sensor 260 may comprise a membrane connected to a piezo-electric sensor that measures displacement of the membrane due to the applied pressure. The membrane may have a width of between 10 µm and 200 µm and a thickness of between 10 µm and 20 µm. The membrane may be formed as silicon. A plurality of pressure sensors 260 may be provided e.g. arranged in a linear array matching the shape of the inspected object, for example the shape of openings in the undersurface of the liquid confinement structure 12. The shape may be circular, elliptical, or a shape with at least one corner. In an embodiment the shape is square, spline or star shaped. In an embodiment the pressure sensors may be arranged in a pattern corresponding to part of the shape of the inspected feature, such as a line corresponding to a side of the shape. The arrangement of pressure sensors 260 can be optimized to the structure of the object to be inspected, e.g. the gas seal.

An inspection substrate according to an embodiment of the present invention can be provided with both one or more imaging devices 210 and one or more pressure sensors 260 in order to enable simultaneous capturing of images and measurement of pressure. Other relevant forms of sensors can be included such as temperature sensors and strain gauges.

FIG. 13 depicts a method of use of the inspection substrate IW to inspect internal functional subsystems, such as the liquid confinement system, of the lithographic apparatus without opening the lithographic apparatus. Therefore, the downtime required for inspection is greatly reduced and the risk of further contamination avoided. Inspection substrate IW is loaded S1 into the lithographic apparatus in exactly the same way as a resist-coated substrate (or production substrate) is loaded for exposure. Inspection substrate IW is placed onto substrate table WT by a substrate handler.

Once loaded into the lithographic apparatus and placed on the substrate table WT, inspection substrate IW may be subjected to certain prequalification steps S2, e.g. flatness measurements, to validate the inspection substrate IW and verify that it will not damage the lithographic apparatus. However a complete pre-characterization and temperature conditioning process as normally performed for production substrates need not be applied.

After any initial steps, the inspection substrate IW is positioned by substrate table WT so that the imaging device 210 is positioned underneath and facing the functional subsystem to be inspected, e.g. the lower surface of immersion liquid confinement structure 12. In positioning the inspection substrate on the substrate table WT, the inspection substrate is orientated in a preferred direction, for example so that sensor devices on the substrate are appropriately orientated with respect to features of the inspected object, such as the openings in the undersurface of the liquid confinement structure 12. In a lithographic apparatus with separate measurement and exposure stations, this may involve a transfer S3 of the inspection substrate IW to the exposure station. Illuminating device 220 is turned on to illuminate the object to be inspected and imaging device 210 captures images S4 of the object to be inspected. Alternatively or in addition, pressure measurements from pressure sensor 260 are recorded. Captured images, which may be in the form of a sequence of still images, or a moving image, and/or pressure measurements are stored in storage device 230. Inspection substrate IW can be stepped or scanned S5 underneath the object to be inspected during the inspection process so as to take images of different parts of the object to be inspected.

During the inspection process the liquid confinement system may be inoperative, partially operative or wholly operative. For example, the liquid confinement system may be inoperative and no immersion liquid present during an inspection using imaging device 210 so that unobscured images of the lower surface of the liquid confinement structure 12 can be obtained. When an inspection process involving pressure measurements is performed, it is desirable that the gas seal and other gas supplies and extraction systems are operative but immersion liquid may or may not be present.

If the inspection substrate IW is resistant to the immersion liquid then an inspection using images can be carried out whilst immersion liquid is present and confined by the liquid confinement system. Such an inspection may not provide clear images of a liquid confinement structure 12 but may instead provide useful images showing the behavior of immersion liquid in the apparatus.

Once all desired images and/or measurements have been collected, inspection substrate IW is unloaded S7 from the apparatus in the same way as a production substrate. However rather than being sent to a track for processing, inspection substrate IW is transferred S8 to a download station 600. At the download station 600 data of the stored images and/or measurements can be downloaded S9 from storage device 230 via control system and interface 240. Control system and interface 240 may connect to the download station via a wireless communication technique, such as Wi-Fi™ or Bluetooth™. Power storage device 250 can be recharged at the download station, e.g. via a wireless induction charging system. Alternatively, the lower surface of inspection substrate IW can be provided with electrical contacts for both downloading of data of images and/or measurements from storage device 230 and for charging power storage device 250.

The downloaded data is then analyzed S10 to identify any faults or problems with the object that has been inspected, for example contamination (such as a blocked opening) in the case of the undersurface of a liquid confinement structure 12. Analysis of the downloaded data can be manual, automatic or a combination of manual and automatic processes. Automatic analysis may include pattern recognition or comparison with reference data, e.g. images of a clean and properly functioning object. If it is decided S11 that a problem exists then remedial action S12 is taken. Remedial action to be taken will depend on the detected problem. If contamination is detected, a cleaning process can be performed. The cleaning process may require decommissioning and opening of the lithographic apparatus for a manual clean or an integrated cleaning device can be used. In some circumstances, e.g. a blockage of a gas seal aperture 151, a flushing operation in which liquid or gas is caused to flow in the opposite to normal direction can be sufficient to remove the contaminant and rectify the problem. After completion of any remedial action, it is decided S13 whether a re-inspection of the object is required and if so the process repeats.

In an embodiment of the present invention, the inspection substrate is used with a lithographic apparatus which has not been designed with the inspection substrate in mind. The lithographic apparatus may have no specific provided means to communicate with or control the inspection substrate when it is in lithographic apparatus. Therefore, the inspection substrate desirably operates autonomously. In an embodiment of the present invention, the inspection substrate is configured to capture images and/or record measurements as soon as it is switched on prior to loading into the lithographic apparatus. The inspection substrate may continue to capture images and/or record measurements until it is unloaded and connected to the download station 600. This may however require a storage device 230 with a very large capacity or may require the sampling rate and/or resolution of captured images to be limited.

In an embodiment, the inspection substrate is programmed to capture images or record measurements for specific time periods which may be defined relative to an included clock or an initiating event. The time periods for image capture and/or measurement recording are predetermined to match the timings of a predetermined program of movements of the inspection substrate through the lithographic apparatus.

In an embodiment, the inspection substrate is configured to determine when it is correctly located to begin capturing images and/or measurements. For example, the controller 500 can be configured to monitor the image detected by the imaging device 210 or the pressure detected by pressure sensor 260. Other sensors can be provided to enable the inspection substrate to determine its location within the lithographic apparatus. For example an acceleration sensor, e.g. a MEMS sensor, can be provided in the inspection substrate to detect movements of the inspection substrate IW and so synchronize measurements and/or imaging with the detected movements.

In an embodiment, the lithographic apparatus is provided with a communication device for communicating with the inspection substrate when the inspection substrate is loaded on the substrate table. The communication means may be a wireless communication means, e.g. Wi-Fi™ or Bluetooth™ or a wired connection via the underside of the inspection substrate. If a wired connection can be provided, power may also be provided to the inspection substrate avoiding the need to provide a power storage device 250 in the inspection substrate. A communication device can be retrofitted to an existing lithographic apparatus.

If a communication device is provided in the lithographic apparatus it can be used to instruct the inspection substrate to begin capturing images and/or other measurements. The communication device can be used to download captured images and measurement data. In an embodiment, data captured by the inspection substrate is downloaded and analyzed in parallel with the scanning of the object to be inspected. This allows remedial action, e.g. a flushing operation, to be carried out immediately upon detection of a problem. A re-scan can then be performed minimizing the downtime required for an inspection.

Although the present invention has been described above in relation to use of the inspection substrate to inspect a functional subsystem of a lithographic apparatus, the inspection substrate can also be used to inspect a functional subsystem of another apparatus, such as a metrology apparatus. An inspection substrate according to an embodiment of the present invention can be used in a process device of the track provided that the inspection substrate is capable of withstanding conditions prevailing in the track, e.g. high temperatures and application of materials such as coatings. An inspection substrate according to an embodiment can be used in a test bed or partial apparatus.

Although specific reference may be made in this text to the use of lithographic apparatus in the manufacture of ICs, it should be understood that the lithographic apparatus described herein may have other applications, such as the manufacture of integrated optical systems, guidance and detection patterns for magnetic domain memories, flat-panel displays, liquid-crystal displays (LCDs), thin film magnetic heads, etc. The skilled artisan will appreciate that, in the context of such alternative applications, any use of the terms "wafer" or "die" herein may be considered as synonymous with the more general terms "substrate" or "target portion", respectively. The substrate referred to herein may be processed, before or after exposure, in for example a track (a tool that typically applies a layer of resist to a substrate and develops the exposed resist), a metrology tool and/or an inspection tool. Where applicable, the disclosure herein may be applied to such and other substrate processing tools. Further, the substrate may be processed more than once, for example in order to create a multi-layer IC, so that the term substrate used herein may also refer to a substrate that already contains one or multiple processed layers.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The terms "radiation" and "beam" used herein encompass all types of electromagnetic radiation, including ultraviolet (UV) radiation (e.g. having a wavelength of or about 436, 405, 365, 248, 193, 157 or 126 nm). and extreme ultra-violet (EUV) radiation (e.g. having a wavelength in the range of 5-20 nm), as well as particle beams, such as ion beams or electron beams.

The term "lens", where the context allows, may refer to any one or combination of various types of optical components, including refractive reflective, magnetic, electromagnetic and electrostatic optical components.

While specific embodiments of the invention have been described above, it will be appreciated that the invention may be practiced otherwise than as described.

Any controllers described herein may each or in combination be operable when the one or more computer programs are read by one or more computer processors located within at least one component of the lithographic apparatus. The controllers may each or in combination have any suitable configuration for receiving, processing, and sending signals. One or more processors are configured to communicate with the at least one of the controllers. For example, each controller may include one or more processors for executing the computer programs that include machine-readable instructions for the methods described above. The controllers may include data storage media for storing such computer programs, and/or hardware to receive such media. So the controller(s) may operate according the machine readable instructions of one or more computer programs.

One or more embodiments of the invention may be applied to any immersion lithography apparatus, in particular, but not exclusively, those types mentioned above and whether the immersion liquid is provided in the form of a bath, only on a localized surface area of the substrate, or is unconfined. In an unconfined arrangement, the immersion liquid may flow over the surface of the substrate and/or substrate table so that substantially the entire uncovered surface of the substrate table and/or substrate is wetted. In such an unconfined immersion system, the liquid supply system may not confine the immersion liquid or it may provide a proportion of immersion liquid confinement, but not substantially complete confinement of the immersion liquid.

A liquid supply system as contemplated herein should be broadly construed. In certain embodiments, it may be a mechanism or combination of structures that provides an immersion liquid to a space between the projection system and the substrate and/or substrate table. It may comprise a combination of one or more structures, one or more fluid openings including one or more liquid openings, one or more gas openings or one or more openings for two phase flow. The openings may each be an inlet into the immersion space (or an outlet from a fluid handling structure) or an outlet out of the immersion space (or an inlet into the fluid handling structure). In an embodiment, a surface of the space may be a portion of the substrate and/or substrate table, or a surface of the space may completely cover a surface of the substrate and/or substrate table, or the space may envelop the substrate and/or substrate table. The liquid supply system may optionally further include one or more elements to control the position, quantity, quality, shape, flow rate or any other features of the immersion liquid.

In an embodiment there is provided an inspection substrate for inspecting a component of an apparatus for processing production substrates, the inspection substrate comprising: a body having dimensions similar to a production substrate so that the inspection substrate is compatible with the apparatus; a sensor for generating inspection information relating to a parameter of a component of the apparatus proximate to the inspection substrate, the sensor embedded in the body; and a storage device embedded in the body, the storage device configured to store the inspection information.

The inspection substrate may comprise a plurality of sensors embedded in the body. The plurality of sensors may be configured to inspect a functional subsystem adjacent to the inspection substrate. The plurality of sensors may generate inspection information.

The or each sensor may comprise an imaging device and the inspection information comprises image data. The imaging device may comprise a plurality of image sensing elements arranged in a two-dimensional array and a microlens for focusing an image of a part of the functional subsystem on the image sensing elements. The microlens may comprise a plurality of lens surfaces, each lens surface forming a separate image of a part of the functional subsystem on image sensing elements. Alternatively or additionally, the imaging device may comprise a plurality of image sensing elements arranged in a two-dimensional array and a plurality of microlenses for focusing radiation on respective ones of the image sensing elements.

The inspection substrate may comprise an illumination device embedded in the body. The illumination device may comprise a plurality of light emitting diodes or laser diodes disposed around the imaging device.

The sensor comprises a pressure sensor. In an embodiment, the inspection substrate may comprise a plurality of pressure sensors spaced apart in an array. The array may be two-dimensional.

In an embodiment there is provided a method of inspecting a component of an apparatus for processing production substrates, the method comprising: loading into the apparatus an inspection substrate having dimensions similar to a production substrate so that the inspection substrate is compatible with the apparatus, the inspection substrate having a body, a sensor and a storage device, the sensor and the storage device being embedded in the body; positioning the inspection substrate proximate the component whilst operating the sensor to generate inspection information relating to a parameter of the component; and storing the inspection information in the storage device. The apparatus may be a lithographic apparatus. The component may be a fluid handling system, in particular a liquid confinement structure. The inspection substrate may comprise a plurality of sensors spaced apart by a distance less than or equal to a dimension of the component.

The component may be a liquid confinement structure having a linear array of fluid openings and the sensor comprises one or more image sensors having a combined field of view having a width in a direction perpendicular to the linear array of fluid openings that is greater than a width of a fluid opening. Alternatively or additionally, the component may be a liquid confinement structure having a first side and a second side spaced apart by a first distance and the inspection substrate comprises a further sensor, the sensor and the further sensor being spaced apart by the first distance. The functional subsystem may be at least partly operating during the scanning.

The method may comprise unloading the inspection substrate from the apparatus and downloading the inspection information from the storage device.

The descriptions above are intended to be illustrative, not limiting. Thus, it will be apparent to one skilled in the art that modifications may be made to the invention as described without departing from the scope of the claims set out below.

The invention claimed is:

1. An inspection substrate for inspecting a component of an apparatus for processing production substrates, the inspection substrate comprising:
 a body having dimensions similar to a production substrate so that the inspection substrate is compatible with the apparatus;
 an illumination device embedded in the body;
 a sensor embedded in the body, the sensor configured to generate inspection information relating to a parameter of a component of the apparatus proximate to the inspection substrate; and
 a storage device embedded in the body, the storage device configured to store the inspection information,
 wherein the sensor comprises an imaging device and the inspection information comprises image data.

2. The inspection substrate of claim 1, further comprising a plurality of sensors embedded in the body and configured to inspect a functional subsystem adjacent to the inspection substrate and to generate inspection information.

3. The inspection substrate of claim 1, wherein the imaging device comprises a plurality of image sensing elements arranged in a two-dimensional array and a microlens configured to focus an image of a part of the functional subsystem on the image sensing elements.

4. The inspection substrate of claim 3, wherein the microlens comprises a plurality of lens surfaces, each lens surface of the plurality of lens surfaces forming a separate image of a part of the functional subsystem on image sensing elements.

5. The inspection substrate of claim 1, wherein the imaging device comprises a plurality of image sensing elements arranged in a two-dimensional array and a plurality of microlenses configured to focus radiation on respective ones of the image sensing elements.

6. The inspection substrate of claim 1, wherein the illumination device comprises a plurality of light emitting diodes or laser diodes disposed around the imaging device.

7. The inspection substrate of claim 1, wherein the sensor further comprises a pressure sensor.

* * * * *